US012614770B2

(12) United States Patent
Kim

(10) Patent No.: US 12,614,770 B2
(45) Date of Patent: Apr. 28, 2026

(54) BATTERY MONITORING DEVICE, BATTERY MONITORING METHOD, BATTERY PACK, AND ELECTRIC VEHICLE

(71) Applicant: LG Energy Solution, Ltd., Seoul (KR)

(72) Inventor: Won-Gon Kim, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 537 days.

(21) Appl. No.: 18/025,768

(22) PCT Filed: Sep. 10, 2021

(86) PCT No.: PCT/KR2021/012372
§ 371 (c)(1),
(2) Date: Mar. 10, 2023

(87) PCT Pub. No.: WO2022/055310
PCT Pub. Date: Mar. 17, 2022

(65) Prior Publication Data
US 2023/0352753 A1 Nov. 2, 2023

(30) Foreign Application Priority Data

Sep. 14, 2020 (KR) ........................ 10-2020-0117920

(51) Int. Cl.
*H01M 10/48* (2006.01)
*B60L 50/64* (2019.01)
(Continued)

(52) U.S. Cl.
CPC ........... *H01M 10/482* (2013.01); *B60L 50/64* (2019.02); *G01N 33/0009* (2013.01);
(Continued)

(58) Field of Classification Search
CPC ............. H01M 10/482; H01M 10/486; H01M 10/488; H01M 10/48; H01M 2220/20;
(Continued)

(56) References Cited

U.S. PATENT DOCUMENTS

2016/0144849 A1* 5/2016 Minamikawa .......... B60L 50/16
180/65.265
2016/0268660 A1 9/2016 Oh
(Continued)

FOREIGN PATENT DOCUMENTS

CN 108258345 A 7/2018
CN 111260875 A 6/2020
(Continued)

OTHER PUBLICATIONS

Extended European Search Report including Written Opinion for Application No. 21867175.8 dated Jan. 19, 2024, pp. 1-6.
(Continued)

*Primary Examiner* — Raymond Alejandro
(74) *Attorney, Agent, or Firm* — Lerner David LLP

(57) ABSTRACT

A battery monitoring apparatus includes a first air quality sensor to generate a first detection signal indicating a concentration of a first material in an internal space of a battery assembly in which at least one battery cell is positioned, a second air quality sensor to generate a second detection signal indicating a concentration of a second material in the internal space, and a controller to execute a first monitoring mode for collecting the first detection signal in first time series in response to an operation start command. The controller executes a second monitoring mode for collecting the second detection signal in second time series in response to the concentration of the first material indicated by the first detection signal exceeding a first threshold during the execution of the first monitoring mode.

11 Claims, 4 Drawing Sheets

(51) Int. Cl.
   *G01N 33/00*          (2006.01)
   *G01R 31/382*        (2019.01)
   *H02J 7/00*            (2006.01)
(52) U.S. Cl.
   CPC ........ *G01R 31/382* (2019.01); *H01M 10/486*
              (2013.01); *H02J 7/0047* (2013.01); *H01M*
                                   *2220/20* (2013.01)
(58) Field of Classification Search
   CPC ... G01R 31/382; B60L 50/64; G01N 33/0009;
                                         H02J 7/0047
   See application file for complete search history.

(56)                References Cited

U.S. PATENT DOCUMENTS

| | | | |
|---|---|---|---|
| 2018/0003685 A1 | 1/2018 | Cummings et al. |
| 2019/0319316 A1 | 10/2019 | Fifield |
| 2019/0379030 A1 | 12/2019 | Golubkov |
| 2020/0052355 A1* | 2/2020 | Kosteva .................. B60L 50/64 |
| 2020/0339010 A1* | 10/2020 | Villanueva ............ B60L 3/0092 |
| 2020/0386816 A1 | 12/2020 | Jeong et al. |

FOREIGN PATENT DOCUMENTS

| | | |
|---|---|---|
| JP | 2019221130 A | 12/2019 |
| KR | 20160109401 A | 9/2016 |
| KR | 20190082540 A | 7/2019 |
| KR | 20190105218 A | 9/2019 |
| KR | 102051809 B1 | 12/2019 |
| KR | 20190139134 A | 12/2019 |
| KR | 102134707 B1 | 7/2020 |
| WO | 2020172427 A1 | 8/2020 |

OTHER PUBLICATIONS

International Search Report for PCT/KR2021/012372 mailed Dec. 13, 2021. 3 pgs.

* cited by examiner

FIG. 2

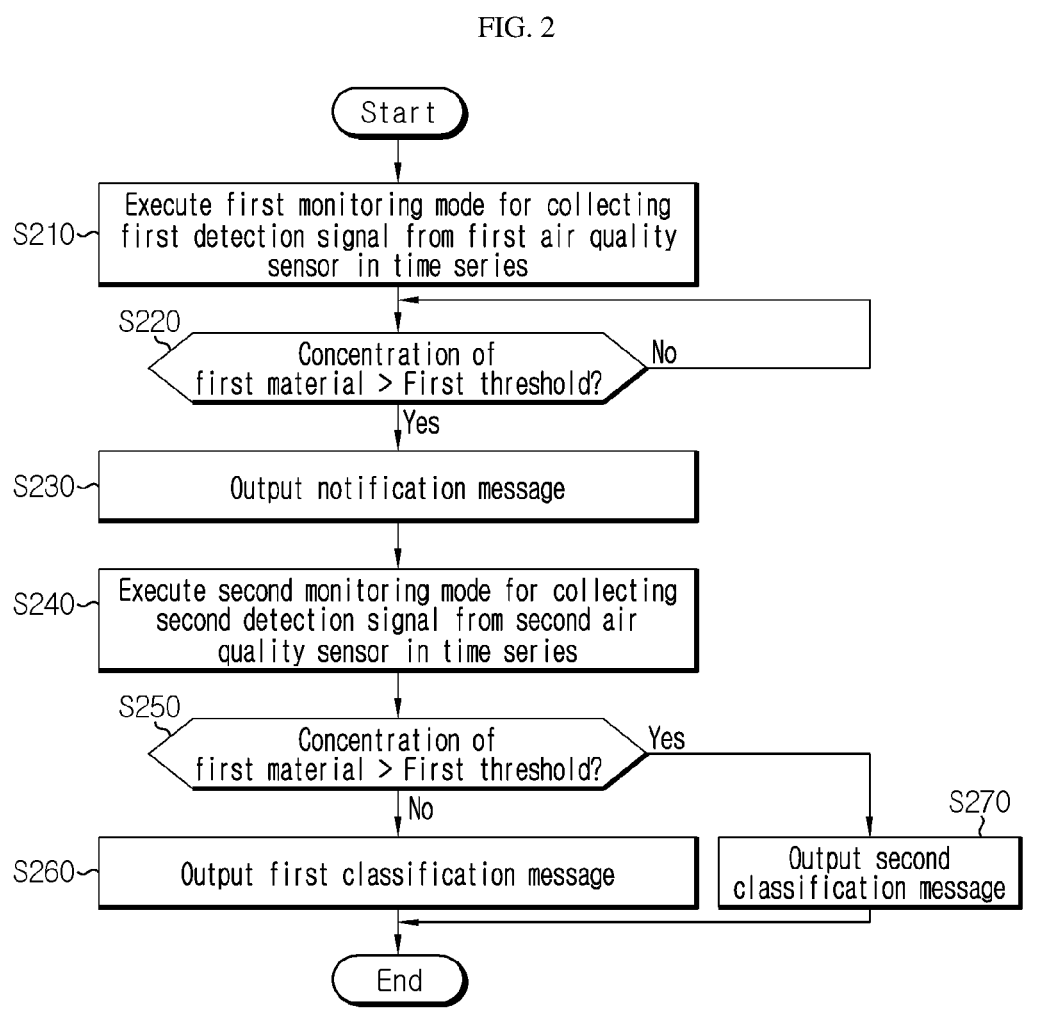

```
                    ┌──────────┐
                    │  Start   │
                    └────┬─────┘
                         │
         ┌───────────────▼────────────────────┐
         │ Execute first monitoring mode for   │
S210─    │ collecting first detection signal   │
         │ from first air quality sensor in    │
         │ time series                         │
         └───────────────┬────────────────────┘
                         │
     S220                │◄──────────────────────┐
       ╱────────────────▼──────────────╲  No     │
      ╱    Concentration of              ╲───────┘
      ╲  first material > First threshold?╱
       ╲──────────────┬───────────────╱
                     │ Yes
         ┌───────────▼────────────────┐
S230─    │   Output notification message│
         └───────────┬────────────────┘
                     │
         ┌───────────▼────────────────────┐
         │ Execute second monitoring mode  │
S240─    │ for collecting second detection │
         │ signal from second air quality  │
         │ sensor in time series           │
         └───────────┬────────────────────┘
                     │
     S250            │
       ╱─────────────▼───────────────╲  Yes
      ╱   Concentration of            ╲──────────┐
      ╲ first material > First threshold?╱        │
       ╲────────────┬──────────────╱             │
                   │ No                    S270  │
         ┌─────────▼─────────────┐    ┌──────────▼──────┐
S260─    │ Output first           │    │ Output second   │
         │ classification message │    │ classification  │
         │                        │    │ message         │
         └─────────┬──────────────┘    └────────┬────────┘
                   │                            │
                   └────────────┬───────────────┘
                          ┌─────▼─────┐
                          │    End    │
                          └───────────┘
```

FIG. 4

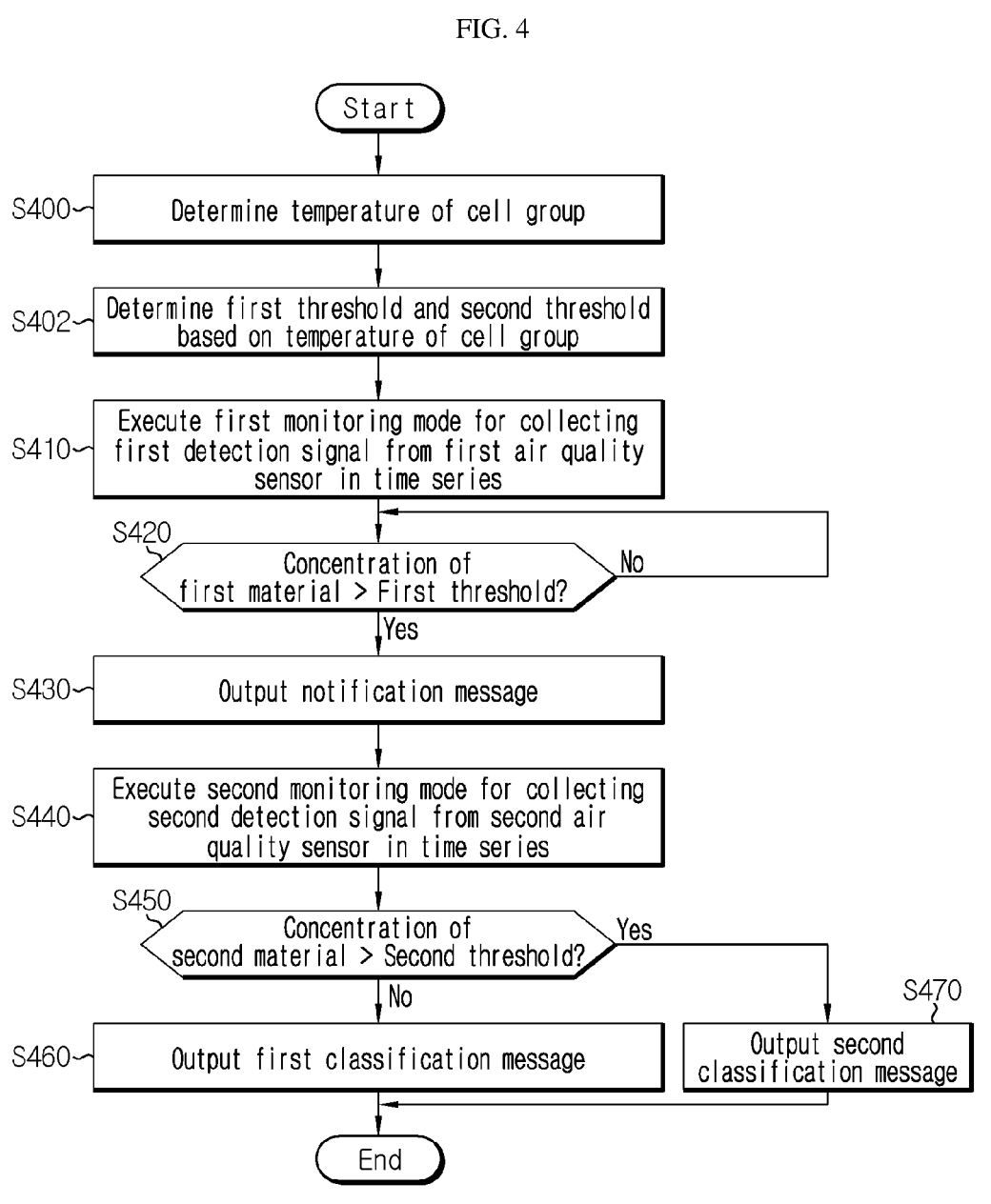

```
                    ┌──────────┐
                    │  Start   │
                    └────┬─────┘
                         │
S400 ─┐  ┌───────────────▼────────────────┐
      └──│  Determine temperature of cell group │
         └───────────────┬────────────────┘
                         │
S402 ─┐  ┌───────────────▼────────────────┐
      └──│ Determine first threshold and second threshold │
         │   based on temperature of cell group │
         └───────────────┬────────────────┘
                         │
S410 ─┐  ┌───────────────▼────────────────┐
      └──│ Execute first monitoring mode for collecting │
         │ first detection signal from first air quality │
         │        sensor in time series │
         └───────────────┬────────────────┘
```

S420 — Concentration of first material > First threshold?    No

Yes

S430 — Output notification message

S440 — Execute second monitoring mode for collecting second detection signal from second air quality sensor in time series S450 — Concentration of second material > Second threshold?    Yes No S460 — Output first classification message S470 — Output second classification message End

BATTERY MONITORING DEVICE, BATTERY MONITORING METHOD, BATTERY PACK, AND ELECTRIC VEHICLE

CROSS-REFERENCE TO RELATED APPLICATION

The present application is a national phase entry under 35 U.S.C. § 371 of International Application No. PCT/KR2021/012372 filed Sep. 10, 2021 which claims prior to Korean Patent Application No. 10-2020-0117920 filed on Sep. 14, 2020 in the Republic of Korea, the disclosures of which are incorporated herein by reference.

TECHNICAL FIELD

The present disclosure relates to technology that monitors whether or not a battery is broken.

BACKGROUND ART

Recently, there has been a rapid increase in the demand for portable electronic products such as laptop computers, video cameras and mobile phones, and with the extensive development of electric vehicles, accumulators for energy storage, robots and satellites, many studies are being made on high performance batteries that can be recharged repeatedly.

Currently, commercially available batteries include nickel-cadmium batteries, nickel-hydrogen batteries, nickel-zinc batteries, lithium batteries and the like, and among them, lithium batteries have hale or no memory effect, and thus they, are gaining more attention than nickel-based batteries for their advantages that recharging can be done whenever it is convenient, the self-discharge rate is very low and the energy density is high.

A battery pack includes a housing and at least one battery cell positioned in an internal space of the housing. The battery cell is manufactured by receiving an electrode stack and an electrolyte in a case, and sealing the case. Since the case isolates the electrode assembly and the electrolyte from the external environment, it is possible to keep the battery cell safe.

In case that the case of the battery cell is broken, a variety of hazardous materials contained in the case may leak from the case.

SUMMARY

Technical Problem

The present disclosure is designed to solve the above-described problem, and therefore the present disclosure is directed to providing an apparatus and method for directly monitoring whether a case of a battery cell is broken based on detection values from different types of air quality sensors positioned in the battery pack, a battery pack comprising the apparatus and an electric vehicle comprising the battery pack.

The present disclosure is further directed to providing an apparatus and method for identifying the cause of the breakage of the case of the battery cell based on the detection values from different types of air quality sensors, a battery pack comprising the apparatus and an electric vehicle comprising the battery pack.

The present disclosure is further directed to providing an apparatus and method for selectively operating any one of different types of air quality sensors according to the detection value of the other air quality sensor, to reduce the power consumption compared to when different types of air quality sensors are always in operation, a battery pack comprising the apparatus and an electric vehicle comprising the battery pack.

These and other objects and advantages of the present disclosure may be understood by the following description and will be apparent from the embodiments of the present disclosure. In addition, it will be readily understood that the objects and advantages of the present disclosure may be realized by the means set forth in the appended claims and a combination thereof.

Technical Solution

A battery monitoring apparatus according to an aspect of the present disclosure is for a battery assembly having an internal space for accommodating at least one battery cell. The battery monitoring apparatus includes a first air quality sensor configured to generate a first detection signal indicating a first concentration of a first material in the internal space, a second air quality sensor configured to generate a second detection signal indicating a second concentration of a second material in the internal space, and a controller is configured to execute a first monitoring mode for collecting the first detection signal in first time series in response to an operation start command. The controller is configured to execute a second monitoring mode for collecting the second detection signal in the second time series in response to the concentration of the first material indicated by the first detection signal exceeding a first threshold during the execution of the first monitoring mode. The first material is produced by evaporation of a reactant required for a charge/discharge reaction of the battery cell. The second material is produced as a by-product of the charge/discharge reaction of the battery cell.

The controller may be configured to determine that a casing of the battery cell is broken in response to the concentration of the first material indicated by the first detection signal exceeding the first threshold during the execution of the first monitoring mode.

The battery monitoring apparatus may further include a power circuit configured to generate a power voltage required for operation of the first air quality sensor and the second air quality sensor.

The controller may be configured to control the power circuit to supply the power voltage to the first air quality sensor in response to the operation start command.

The controller may be configured to control the power circuit to supply the power voltage to the second air quality sensor in response to the concentration of the first material indicated by the first detection signal exceeding the first threshold.

The controller may be configured to determine that a casing of the battery cell is broken by an external cause in response to the concentration of the second material indicated by the second detection signal being equal to or less than a second threshold during the execution of the second monitoring mode.

The controller may be configured to determine that a casing of the battery cell is broken by an internal cause in response to the concentration of the second material indicated by the second detection signal exceeding a second threshold during the execution of the second monitoring mode.

A battery pack according to another aspect of the present disclosure include the battery monitoring apparatus.

An electric vehicle according to still another aspect of the present disclosure includes the battery pack.

A battery monitoring method according to yet another aspect of the present disclosure uses a first air quality sensor configured to generate a first detection signal indicating a concentration of a first material in an internal space of a battery assembly in which at least one battery cell is positioned; and a second air quality sensor configured to generate a second detection signal indicating a concentration of a second material in the internal space. The battery monitoring method includes executing, by a controller, a first monitoring mode for collecting the first detection signal in first time series in response to an operation start command, and executing, by the controller, a second monitoring mode for collecting the second detection signal in second time series in response to the concentration of the first material indicated by the first detection signal exceeding a first threshold during the execution of the first monitoring mode. The first material is produced by evaporation of a reactant required for a charge/discharge reaction of the battery cell included in the battery assembly. The second material is produced as a by-product of the charge/discharge reaction of the battery cell.

The battery monitoring method may further include determining that a casing of the battery cell is broken by an external cause in response to the concentration of the second material indicated by the second detection signal being equal to or less than a second threshold during the execution of the second monitoring mode.

The battery monitoring method may further include determining that the casing of the battery cell is broken by an internal cause in response to the concentration of the second material indicated by the second detection signal exceeding a second threshold during the execution of the second monitoring mode.

Advantageous Effects

According to at least one of the embodiments of the present disclosure, it is possible to directly monitor whether the case of the battery cell is broken based on the detection values from different types of air quality sensors positioned in the battery pack.

Additionally, according to at least one of the embodiments of the present disclosure, it is possible to identify the cause of the breakage of the case of the battery cell based on the detection values from different types of air quality sensors.

Furthermore, according to at least one of the embodiments of the present disclosure, it is possible to reduce the power consumption compared to when different types of air quality sensors are always in operation, by selectively operating any one of different types of air quality sensors according to the detection value of the other air quality sensor.

The effects of the present disclosure are not limited to the effects mentioned above, and these and other effects will be clearly understood by those skilled in the art from the appended claims.

BRIEF DESCRIPTION OF THE DRAWINGS

The accompanying drawings illustrate a preferred embodiment of the present disclosure, and together with the detailed description of the present disclosure described below, serve to provide a further understanding of the technical aspects of the present disclosure, and thus the present disclosure should not be construed as being limited to the drawings.

FIG. 2 illustrates exemplarily a flowchart of a battery monitoring method according to a second embodiment that is executable by a battery monitoring apparatus of FIG. 1.

FIG. 4 illustrates exemplarily a flowchart of a battery monitoring method according to a third embodiment that is executable by a battery monitoring apparatus of FIG. 1.

DETAILED DESCRIPTION

Figure 1:
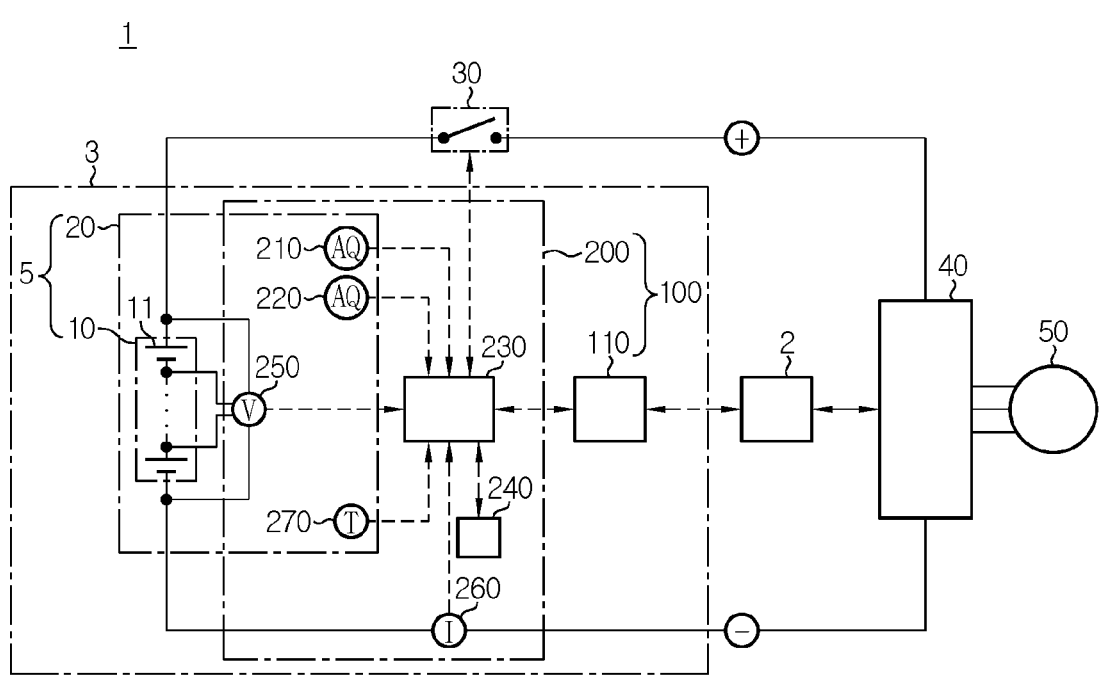
FIG. 1 is an exemplary diagram illustrating a configuration of an electric vehicle according to the present disclosure.

Hereinafter, the preferred embodiments of the present disclosure will be described in detail with reference to the accompanying drawings. Prior to the description, it should be understood that the terms or words used in the specification and the appended claims should not be construed as being limited to general and dictionary meanings, but rather interpreted based on the meanings and concepts corresponding to the technical aspects of the present disclosure on the basis of the principle that the inventor is allowed to define the terms appropriately for the best explanation.

Therefore, the embodiments described herein and the illustrations shown in the drawings are just a most preferred embodiment of the present disclosure, but not intended to fully describe the technical aspects of the present disclosure, so it should be understood that a variety of other equivalents and modifications could have been made thereto at the time that the application was filed.

The terms including the ordinal number such as "first", "second" and the like, are used to distinguish one element from another among various elements, but not intended to limit the elements by the terms.

Unless the context clearly indicates otherwise, it will be understood that the term "comprises" when used in this specification, specifies the presence of stated elements, but does not preclude the presence or addition of one or more other elements. Additionally, the term "control unit" refers to a processing unit of at least one function or operation, and this may be implemented by hardware and software either alone or in combination.

In addition, throughout the specification, it will be further understood that when an element is referred to as being "connected to" another element, it can be directly connected to the other element or intervening elements may be present.

FIG. 1 is an exemplary diagram illustrating a configuration of an electric vehicle 1 according to the present disclosure.

Referring to FIG. 1, the electric vehicle 1 includes a high-level controller 2, a battery pack 3, a switch 30, an inverter 40 and an electric motor 50.

The battery pack 3 includes a battery assembly 5 and a battery management system 100.

The switch 30 is electrically connected in series to the battery assembly 5 through a power path connecting the battery assembly 5 to the inverter 40. The on-off control of the switch 30 is performed in response to a switching signal from the battery management system 100. The switch 30 may be a mechanical relay that is turned on/off by the electromagnetic force of a coil or the semiconductor switch 30 such as Metal Oxide Semiconductor Field Effect transistor (MOSFET).

The inverter 40 is provided to convert the direct current (DC) from a cell group 10 to the alternating current (AC) in response to a command from the battery management system 100.

The electric motor 50 works using the AC power from the inverter 40. The electric motor 50 may be, for example, a three-phase AC motor 50.

The battery assembly 5 includes the cell group 10 and a housing 20. The housing 20 defines the entire shape of the battery assembly 5 and provides an internal space in which the cell group 10 may be positioned. The housing 20 is fixed and fastened to a battery room provided in the electric vehicle 1 through bolts.

The cell group 10 is positioned (received) in the internal space provided from the housing 20, and includes at least one battery cell 11. When the cell group 10 has the plurality of battery cells 11, the plurality of battery cells 11 may be connected either in series or in parallel, or both. The battery cell 11 may be, for example, a lithium ion battery cell. The battery cell 11 is not limited to a particular type, and may include any battery cell that can be repeatedly recharged. The battery cell 11 includes an electrode stack, an electrolyte and a case. The electrode stack includes a positive electrode plate, a negative electrode plate and a separator. The case provides a hermetic seal for the electrode stack and the electrolyte to prevent the leakage of reactants and by-products of the battery cell 11. The reactant may refer collectively to materials which participate in the charge/discharge reaction of the battery cell 11, such as the positive electrode active material and the negative electrode active material coated on the electrode stack and/or the electrolyte. The by-product may refer collectively to materials which do not participate in the charge/discharge reaction and are produced incidentally from the charge/discharge reaction.

The battery management system 100 includes a battery monitoring apparatus 200 and an interface unit 110.

The battery monitoring apparatus 200 includes a first air quality sensor 210, a second air quality sensor 220 and a control unit 230. The battery monitoring apparatus 200 may further include at least one of a power circuit 240, a voltage sensor 250, a current sensor 260 or a temperature sensor 270. The battery monitoring apparatus 200 is provided to monitor whether the battery cell 11 included in the cell group 10 is broken. The battery monitoring apparatus 200 is configured to determine whether the breakage of the battery cell 11 is caused by an external cause or an internal cause in response to the detected breakage of the battery cell 11.

The power circuit 240 is configured to generate a power voltage required for the activation of the first air quality sensor 210 and the second air quality sensor 220 using the power supplied from an auxiliary power source (for example, a lead acid battery) provided in the cell group 10 or the electric vehicle 1. The power circuit 240 may include, for example, a voltage regulator and a DC-DC converter well known in the technical field. The power circuit 240 may be configured to selectively supply the power voltage to only the first air quality sensor 210 in response to a first command from the control unit 230. The power circuit 240 may be configured to selectively supply the power voltage to only the second air quality sensor 220 in response to a second command from the control unit 230. Alternatively, at least one of the first air quality sensor 210 or the second air quality sensor 220 may be configured to always work using the power from the power source (for example, the coin cell) embedded therein.

The first air quality sensor 210 is positioned in the internal space of the housing 20. The first air quality sensor 210 is configured to detect a first material present in the internal space, and generate a first detection signal indicating the concentration of the first material.

The second air quality sensor 220 is positioned in the internal space of the housing 20. The second air quality sensor 220 is configured to detect a second material present in the internal space, and generate a second detection signal indicating the concentration of the second material.

The first material and the second material are different types of gas materials produced in the internal space of the housing 20 when the case of the battery cell 11 is broken by a certain cause.

Specifically, the first material is a gas material produced by evaporation of the reactant (for example, the electrolyte) directly required for the charge/discharge reaction of the battery cell 11. For example, the first material may be Volatile Organic Compounds (VOCs). The second material is not a reactant of the battery cell 11, and is a gas material produced as a by-product of the charge/discharge reaction of the battery cell 11. For example, the second material may be carbon dioxide ($CO_2$).

The breakage of the battery cell 11 occurs by at least one of the external cause or the internal cause. The external cause refers collectively to causes that are irrelevant to the charge/discharge reaction of the battery cell 11. For example, the external cause may include vibration transmitted from the vehicle body of the electric vehicle 1 to the battery cell 11, and adsorption of a corrosive material onto the case of the battery cell 11. The internal cause refers collectively to causes that are relevant to the charge/discharge reaction of the battery cell 11. For example, the internal cause may include swelling of the case by carbon dioxide accumulated in the case of the battery cell 11.

When the external cause contributes to the breakage of the battery cell 11 more strongly than the internal cause, the reactant of the battery cell 11 leaks from the case. Accordingly, the concentration of the first material in the housing 20 rises fast, but the concentration of the second material is uniformly maintained or shows a very small change before and after the breakage.

In contrast, when the internal cause contributes to the breakage of the battery cell 11 more strongly than the external cause, even the second material accumulated in the case as a by-product of the charge/discharge reaction leaks from the case together with the electrolyte. Accordingly, the concentration of both the first material and the second material present in the internal space of the housing 20 rises fast.

That is, in case that the battery cell 11 is broken, the concentration of the first material in the housing 20 rises fast irrespective of its cause, and as the contribution of the internal cause is higher, the concentration of the second material rises fast. Accordingly, it is possible to monitor whether or not the case of the battery cell 11 is broken from the measured concentration value of the first material, and predict the contribution (high or low contribution) of each of the external cause and the internal cause of the breakage of the case of the battery cell 11 based on the detected concentration value of the second material.

The voltage sensor 250 is electrically connected to two ends of the battery cell 11 through a voltage sensing channel. The voltage sensor 250 is configured to measure a cell 11 voltage across the battery cell 11, and output a signal indicating the cell 11 battery voltage to the control unit 230.

The current sensor 260 is electrically connected in series to the cell group 10 through the power path. For example, the current sensor 260 may include a shunt resistor or a hall effect device. The current sensor 260 is configured to measure a current flowing through the cell group 10, and output a signal indicating the measured current to the control unit 230.

The temperature sensor 270 is positioned in the internal space of the housing 20. For example, the temperature sensor 270 may include a thermocouple. The temperature sensor 270 is configured to measure a temperature of the cell group 10, and output a signal indicating the measured temperature to the control unit 230.

The control unit 230 is operably coupled to the first air quality sensor 210 and the second air quality sensor 220. The control unit 230 may be additionally operably coupled to at least one of the power circuit 240, the voltage sensor 250, the current sensor 260 or the temperature sensor 270.

The control unit 230 may be implemented in hardware using at least one of application specific integrated circuits (ASICs), digital signal processors (DSPs), digital signal processing devices (DSPDs), programmable logic devices (PLDs), field programmable gate arrays (FPGAs), microprocessors or electrical units for performing the other functions. The control unit 230 may include a memory embedded therein. The memory may include, for example, at least one type of storage medium of flash memory type, hard disk type, Solid State Disk (SSD) type, Silicon Disk Drive (SDD) type, multimedia card micro type, random access memory (RAM), static random access memory (SRAM), read-only memory (ROM), electrically erasable programmable read-only memory (EEPROM) or programmable read-only memory (PROM). The memory may pre-store programs and data necessary to perform battery management methods according to embodiments as described below.

The interface unit 110 configured to support wired or wireless communication between the control unit 230 and the high-level controller 2 (for example, an Electronic Control Unit (ECU)) of the electric vehicle 1. The wired communication may be, for example, controller area network (CAN) communication, and the wireless communication may be, for example, Zigbee or Bluetooth communication. The communication protocol is not limited to a particular type, and may include any communication protocol that supports the wired/wireless communication between the control unit 230 and the high-level controller 2. The interface unit 110 may include an output device (for example, a display, a speaker) to provide the information received from the control unit 230 and/or the high-level controller 2 in a recognizable format.

The method of FIGS. 2 and 3 as described below may start when the battery monitoring apparatus 200 changes from a sleep state to a wake-up state. The sleep state may be a state in which the switch 30 is turned off to stop charging/discharging the cell group 10 in response to an operation stop command from the high-level controller 2. In the sleep state, the control unit 230 monitors the state of the cell group 10 in a predetermined cycle (for example, 1 time/1 sec) while waiting for input of an operation start command from the high-level controller 2. The wake-up state may be a state in which the switch 30 is turned on to charge/discharge the cell group 10 in response to the operation start command. In the wake-up state, the control unit 230 monitors the state of the cell group 10 in a predetermined cycle (for example, 1000 times/1 sec) that is shorter than the sleep state.

FIG. 2 illustrates exemplarily a flowchart of a battery monitoring method according to a first embodiment that is executable by the battery monitoring apparatus 200 of FIG. 1.

Referring to FIGS. 1 and 2, in step S210, the control unit 230 executes a first monitoring mode for collecting the first detection signal from the first air quality sensor 210 in time series. During the execution of the first monitoring mode, the control unit 230 may record the detection value of the first air quality sensor 210 in the memory in time series.

In step S220, the control unit 230 determines whether the concentration of the first material indicated by the first detection signal exceeds a first threshold. The first threshold (for example, 2.0 ppm) is a reliable reference value for the breakage of the battery cell 11. The first threshold may be preset considering the number of battery cells 11 included in the cell group 10 and the area of the internal space of the housing 20. When a value of the step S220 is "Yes", step S230 or S240 is performed. When the value of the step S220 is "No", the step S220 may be performed again.

In the step S230, the control unit 230 outputs a notification message indicating the broken case of the battery cell 11. The notification message may be transmitted from the control unit 230 to the high-level controller 2 through the interface unit 110. The step S230 may be optionally omitted from the method of FIG. 2.

In the step S240, the control unit 230 executes a second monitoring mode for collecting the second detection signal from the second air quality sensor 220 in time series. The first monitoring mode may be stopped during the execution of the second monitoring mode, or may be executed in parallel with the second monitoring mode. During the execution of the second monitoring mode, the control unit 230 may record the detection value of the second air quality sensor 220 in the memory in time series.

In step S250, the control unit 230 determines whether the concentration of the second material indicated by the second detection signal exceeds a second threshold. The second threshold (for example, 100.0 ppm) is a reliable reference value for the breakage of the battery cell 11. The second threshold may be preset considering the number of battery cells 11 included in the cell group 10 and the area of the internal space of the housing 20. When a value of the step S250 is "No", step S260 is performed. When the value of the step S250 is "Yes", step S270 is performed.

In the step S260, the control unit 230 outputs a first classification message indicating that the case of the battery cell 11 was broken by the external cause. The first classification message may be transmitted from the control unit 230 to the high-level controller 2 through the interface unit 110.

In the step S270, the control unit 230 outputs a second classification message indicating that the case of the battery cell 11 was broken by the internal cause. The second classification message may be transmitted from the control unit 230 to the high-level controller 2 through the interface unit 110.

Figure 3:
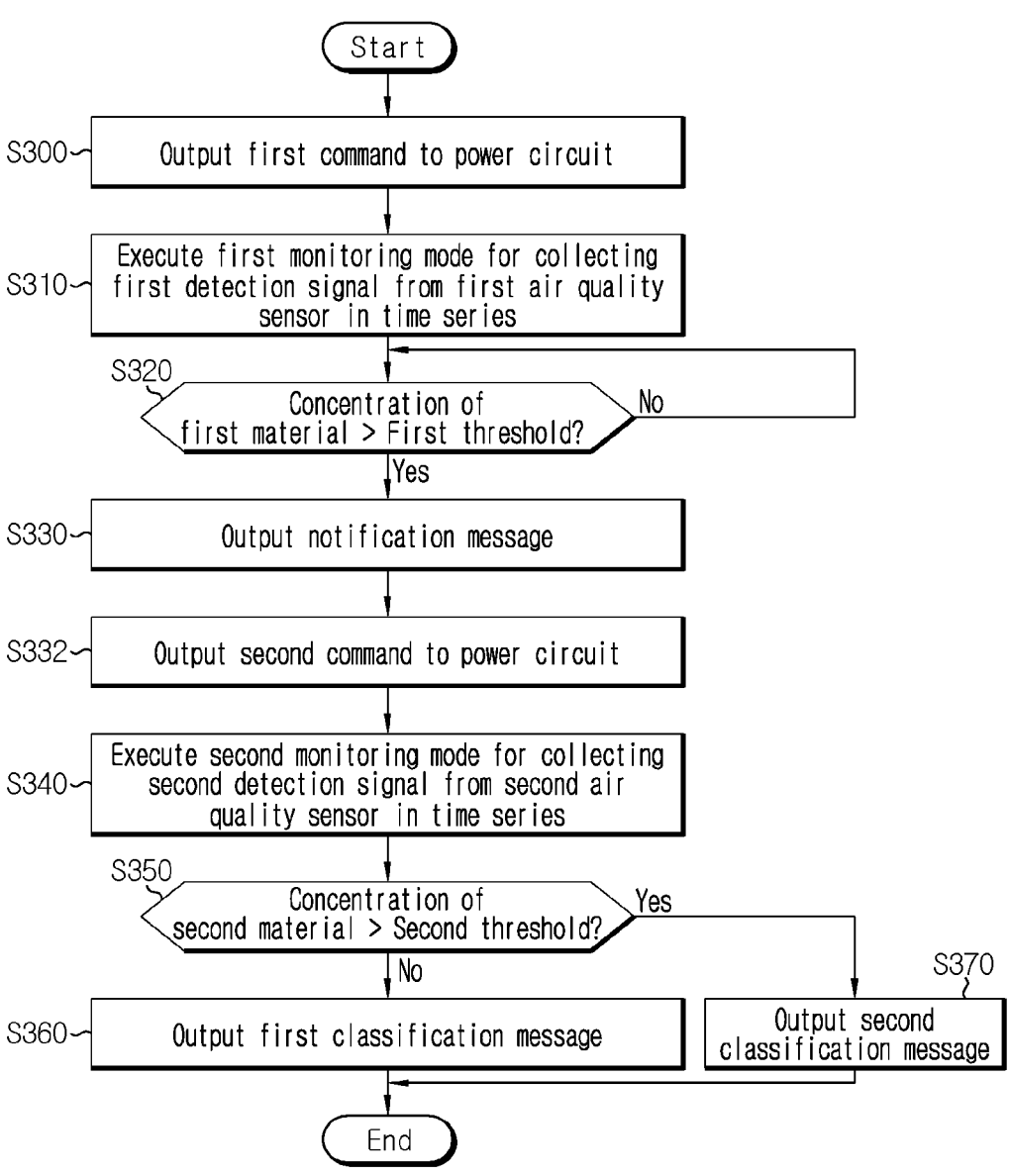
FIG. 3 illustrates exemplarily a flowchart of a battery monitoring method according to a second embodiment that is executable by a battery monitoring apparatus of FIG. 1.

FIG. 3 illustrates exemplarily a flowchart of a battery monitoring method according to a second embodiment that is executable by the battery monitoring apparatus 200 of FIG. 1.

Referring to FIGS. 1 and 3, in step S300, the control unit 230 outputs a first command to the power circuit 240. The power circuit 240 outputs the power voltage to the first air quality sensor 210 in response to the first command. The first air quality sensor 210 changes from an inactive state to an active state by the power voltage and starts detecting the first material.

In step S310, the control unit 230 executes the first monitoring mode for collecting the first detection signal from the first air quality sensor 210 in time series. During the execution of the first monitoring mode, the control unit 230 may periodically record the detection value of the first air quality sensor 210 in the memory.

In step S320, the control unit 230 determines whether the concentration of the first material indicated by the first detection signal exceeds the first threshold. When a value of the step S320 is "Yes", step S330 or S332 is performed. When the value of the step S320 is "No", step S320 may be performed again.

In the step S330, the control unit 230 outputs a notification message indicating the broken case of the battery cell 11. The notification message may be transmitted from the control unit 230 to the high-level controller 2 through the interface unit 110. The step S330 may be optionally omitted from the method of FIG. 3.

In the step S332, the control unit 230 outputs a second command to the power circuit 240. The power circuit 240 outputs the power voltage to the second air quality sensor 220 in response to the second command. The second air quality sensor 220 changes from the inactive state to the active state by the power voltage and starts detecting the second material.

In step S340, the control unit 230 executes the second monitoring mode for collecting the second detection signal from the second air quality sensor 220 in time series. The first monitoring mode may be stopped during the execution of the second monitoring mode, or may be executed in parallel with the second monitoring mode. During the execution of the second monitoring mode, the control unit 230 may record the detection value of the second air quality sensor 220 in the memory in time series.

In step S350, the control unit 230 determines whether the concentration of the second material indicated by the second detection signal exceeds the second threshold. The second threshold (for example, 100.0 ppm) is a reliable reference value for the breakage of the battery cell 11. The second threshold may be preset considering the number of battery cells 11 included in the cell group 10 and the area of the internal space of the housing 20. When a value of the step S350 is "No", step S360 is performed. When the value of the step S350 is "Yes", step S370 is performed.

In the step S360, the control unit 230 outputs the first classification message indicating that the case of the battery cell 11 was broken by the external cause. The first classification message may be transmitted from the control unit 230 to the high-level controller 2 through the interface unit 110.

In the step S370, the control unit 230 outputs the second classification message indicating that the case of the battery cell 11 was broken by the internal cause. The second classification message may be transmitted from the control unit 230 to the high-level controller 2 through the interface unit 110.

FIG. 4 illustrates exemplarily a flowchart of a battery monitoring method according to a third embodiment that is executable by the battery monitoring apparatus 200 of FIG. 1.

Referring to FIGS. 1 and 4, in step S400, the control unit 230 determines the temperature of the cell group 10 based on the signal from the temperature sensor 270.

In step S402, the control unit 230 determines a first threshold and a second threshold based on the temperature of the cell group 10. As opposed to the first and second embodiment, the first threshold and the second threshold of the third embodiment may be a variable value that relies on the temperature of the cell group 10. Even at the equal extent to which the battery cell 11 is broken, as the temperature of the cell group 10 is higher, the concentration of each of the first material and the second material detected as being present in the housing 20 may rise. It is because the reactant is prone to evaporate at high temperature, and the by-product is produced in a larger amount with increasing temperature. The memory may pre-store functions or data tables defining a first correlation between the temperature of the cell group 10 and the first threshold and a second correlation between the temperature of the cell group 10 and the second threshold.

In step S410, the control unit 230 executes the first monitoring mode for collecting the first detection signal from the first air quality sensor 210 in time series. During the execution of the first monitoring mode, the control unit 230 may record the detection value of the first air quality sensor 210 in the memory in time series.

In step S420, the control unit 230 determines whether the concentration of the first material indicated by the first detection signal exceeds the first threshold. When a value of the step S420 is "Yes", step S430 or S440 is performed. When the value of the step S420 is "No", the step S420 may be performed again.

In the step S430, the control unit 230 outputs the notification message indicating the broken case of the battery cell 11. The notification message may be transmitted from the control unit 230 to the high-level controller 2 through the interface unit 110. The step S430 may be optionally omitted from the method of FIG. 2.

In the step S440, the control unit 230 executes the second monitoring mode for collecting the second detection signal from the second air quality sensor 220 in time series. The first monitoring mode may be stopped during the execution of the second monitoring mode, or may be executed in parallel with the second monitoring mode. During the execution of the second monitoring mode, the control unit 230 may record the detection value of the second air quality sensor 220 in the memory in time series.

In step S450, the control unit 230 determines whether the concentration of the second material indicated by the second detection signal exceeds the second threshold. When a value of the step S450 is "No", step S460 is performed. When the value of the step S450 is "Yes", step S470 is performed.

In the step S460, the control unit 230 outputs the first classification message indicating that the case of the battery cell 11 was broken by the external cause. The first classification message may be transmitted from the control unit 230 to the high-level controller 2 through the interface unit 110.

In the step S470, the control unit 230 outputs the second classification message indicating that the case of the battery cell 11 was broken by the internal cause. The second classification message may be transmitted from the control unit 230 to the high-level controller 2 through the interface unit 110.

The first classification message described above with reference to FIGS. 2 to 4 may indicate that the external cause contributes to the breakage of the case of the battery cell 11 more strongly than the internal cause. On the contrary, the second classification message may indicate that the internal cause contributes to the breakage of the case of the battery cell 11 more strongly than the external cause.

The embodiments of the present disclosure described hereinabove are not implemented only through the apparatus and method, and may be implemented through programs that perform functions corresponding to the configurations of the embodiments of the present disclosure or recording media having the programs recorded thereon, and such implementation may be easily achieved by those skilled in the art from the disclosure of the embodiments previously described.

While the present disclosure has been hereinabove described with regard to a limited number of embodiments and drawings, the present disclosure is not limited thereto and it is obvious to those skilled in the art that various modifications and changes may be made thereto within the technical aspects of the present disclosure and the equivalent scope of the appended claims.

Additionally, as many substitutions, modifications and changes may be made to the present disclosure described hereinabove by those skilled in the art without departing from the technical aspects of the present disclosure, the present disclosure is not limited by the above-described embodiments and the accompanying drawings, and some or all of the embodiments may be selectively combined to allow various modifications.

What is claimed is:

1. A battery monitoring apparatus for a battery assembly having an internal space for accommodating at least one battery cell, the battery monitoring apparatus comprising:

a first air quality sensor configured to generate a first detection signal indicating a first concentration of a first material in the internal space;

a second air quality sensor configured to generate a second detection signal indicating a second concentration of a second material in the internal space; and a controller configured to execute a first monitoring mode for collecting the first detection signal in first time series in response to an operation start command, wherein the controller is configured to execute a second monitoring mode for collecting the second detection signal in second time series in response to the concentration of the first material indicated by the first detection signal exceeding a first threshold during the execution of the first monitoring mode, wherein the first material is produced by evaporation of a reactant required for a charge/discharge reaction of the battery cell, and the second material is produced as a by-product of the charge/discharge reaction of the battery cell.

2. The battery monitoring apparatus according to claim 1, wherein the controller is configured to determine that a casing of the battery cell is broken in response to the concentration of the first material indicated by the first detection signal exceeding the first threshold during the execution of the first monitoring mode.

3. The battery monitoring apparatus according to claim 1, further comprising:

a power circuit configured to generate a power voltage required for operation of the first air quality sensor and the second air quality sensor, wherein the controller is configured to control the power circuit to supply the power voltage to the first air quality sensor in response to the operation start command.

4. The battery monitoring apparatus according to claim 3, wherein the controller is configured to control the power circuit to supply the power voltage to the second air quality sensor in response to the concentration of the first material indicated by the first detection signal exceeding the first threshold.

5. The battery monitoring apparatus according to claim 1, wherein the controller is configured to determine that a casing of the battery cell is broken by an external cause in response to the concentration of the second material indicated by the second detection signal being equal to or less than a second threshold during the execution of the second monitoring mode.

6. The battery monitoring apparatus according to claim 1, wherein the controller is configured to determine that a casing of the battery cell is broken by an internal cause in response to the concentration of the second material indicated by the second detection signal exceeding a second threshold during the execution of the second monitoring mode.

7. A battery pack comprising the battery monitoring apparatus according to claim 1.

8. An electric vehicle comprising the battery pack according to claim 7.

9. A battery monitoring method using a first air quality sensor configured to generate a first detection signal indicating a concentration of a first material in an internal space of a battery assembly in which at least one battery cell is positioned; and a second air quality sensor configured to generate a second detection signal indicating a concentration of a second material in the internal space, the battery monitoring method comprising:

executing, by a controller, a first monitoring mode for collecting the first detection signal in first time series in response to an operation start command; and executing, by the controller, a second monitoring mode for collecting the second detection signal in second time series in response to the concentration of the first material indicated by the first detection signal exceeding a first threshold during the execution of the first monitoring mode, wherein the first material is produced by evaporation of a reactant required for a charge/discharge reaction of the battery cell included in the battery assembly, and the second material is produced as a by-product of the charge/discharge reaction of the battery cell.

10. The battery monitoring method according to claim 9, further comprising:

determining that a casing of the battery cell is broken by an external cause in response to the concentration of the second material indicated by the second detection signal being equal to or less than a second threshold during the execution of the second monitoring mode.

11. The battery monitoring method according to claim 9, further comprising:

determining that the casing of the battery cell is broken by an internal cause in response to the concentration of the second material indicated by the second detection signal exceeding a second threshold during the execution of the second monitoring mode.

* * * * *